United States Patent
Wabel et al.

(10) Patent No.: US 9,980,663 B2
(45) Date of Patent: May 29, 2018

(54) METHOD AND ARRANGEMENT FOR DETERMINING AN OVERHYDRATION PARAMETER OR A BODY COMPOSITION PARAMETER

(71) Applicants: Peter Wabel, Darmstadt (DE); Paul Chamney, Herts (GB); Ulrich Moissl, Karben (DE); Sebastian Wieskotten, Ober-Ramstadt (DE)

(72) Inventors: Peter Wabel, Darmstadt (DE); Paul Chamney, Herts (GB); Ulrich Moissl, Karben (DE); Sebastian Wieskotten, Ober-Ramstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 198 days.

(21) Appl. No.: 14/349,182

(22) PCT Filed: Oct. 5, 2012

(86) PCT No.: PCT/EP2012/004182
§ 371 (c)(1),
(2) Date: Apr. 2, 2014

(87) PCT Pub. No.: WO2013/050170
PCT Pub. Date: Apr. 11, 2013

(65) Prior Publication Data
US 2014/0243699 A1    Aug. 28, 2014

Related U.S. Application Data

(60) Provisional application No. 61/544,449, filed on Oct. 7, 2011.

(30) Foreign Application Priority Data

Oct. 7, 2011  (EP) .................................... 11008146

(51) Int. Cl.
A61B 5/053    (2006.01)
A61B 5/00     (2006.01)

(52) U.S. Cl.
CPC .......... *A61B 5/0537* (2013.01); *A61B 5/4875* (2013.01); *A61B 5/6825* (2013.01); *A61B 5/6829* (2013.01)

(58) Field of Classification Search
CPC ... A61B 5/6829; A61B 5/6825; A61B 5/4875; A61B 5/0537
(Continued)

(56) References Cited

U.S. PATENT DOCUMENTS

| | | | |
|---|---|---|---|
| 5,372,141 A | 12/1994 | Gallup et al. | |
| 6,022,322 A * | 2/2000 | Prutchi | A61B 5/4869 600/506 |

(Continued)

FOREIGN PATENT DOCUMENTS

| | | |
|---|---|---|
| JP | 11-505431 | 5/1999 |
| JP | 2007/502675 | 10/2009 |
| WO | WO 2006/002685 | 1/2006 |

*Primary Examiner* — Adam J. Eiseman
(74) *Attorney, Agent, or Firm* — Jacobson Holman, PLLC.

(57) ABSTRACT

A method and an arrangement for determining an overhydration parameter or a body composition parameter are disclosed. The method comprises: obtaining first bioimpedance measurement data of a patient from a first type of bioimpedance measurement (204), deriving bioimpedance calibration data from the first bioimpedance measurement data for calibrating second bioimpedance measurement data from a second type of bioimpedance measurement (205), obtaining the second bioimpedance measurement data from a second bioimpedance measurement of the patient (206), and calibrating the second bioimpedance measurement data
(Continued)

using the calibration data to determine the overhydration parameter or the body composition parameter of the patient (207).

10 Claims, 11 Drawing Sheets

(58) Field of Classification Search
USPC .......................................................... 600/547
See application file for complete search history.

(56) References Cited

U.S. PATENT DOCUMENTS

2005/0070778 A1* 3/2005 Lackey ................ A61B 5/0537
  600/366
2009/0264792 A1* 10/2009 Mazar .................. A61B 5/0531
  600/547

\* cited by examiner

METHOD AND ARRANGEMENT FOR DETERMINING AN OVERHYDRATION PARAMETER OR A BODY COMPOSITION PARAMETER

This is a national stage of PCT/EP12/004182 filed Oct. 5, 2012 and published in English, which has a priority of Europe no. 11008146.0, filed Oct. 7, 2011, and claiming benefit of U.S. provisional No. 61/544,449, filed Oct. 7, 2011, hereby incorporated by reference.

TECHNICAL FIELD

The present invention relates to the field of monitoring or determining the hydration and/or nutrition status of a patient using bioimpedance measurements.

BACKGROUND

The kidneys serve various functions for maintaining a healthy condition of the human body. As one aspect the kidneys control the fluid balance by separating any excess fluid from the blood volume of the patient. Second they serve to purify the blood from waste substances such as urea or creatinin. Further they also control the level of certain substances in the blood such as electrolytes to ensure a healthy and necessary concentration level.

In case of renal failure excess fluid accumulates in body tissue and causes an increasing stress to the circulation/vascular system. This excess fluid has to be withdrawn from the patient using ultrafiltration. If an insufficient amount of fluid is withdrawn, the long term consequences may be severe and may lead to an increased blood pressure and heart failure. The risk of a heart failure is increased for dialysis patients and it is assumed that excess fluid is an important factor for this. Removing an excessive amount of fluid is also dangerous as the dialysis patient will become dehydrated, resulting in a hypotension.

The dry weight (for simplicity the terms weight and mass shall be used synonymously in this application—in correspondence with medical practice) defines the weight of the patient that would be reached, if the kidneys were functioning normally. In other words the dry weight represents the optimum target weight, or the fluid status, that should be reached to minimize the cardiovascular risk. The dry weight has always been a difficult to address problem in clinical practice, as quantitative procedures for determination have not been available. Currently the dry weight is often approached using indirect indicators such as blood pressure, echocardiography, and subjective information such as X-ray imaging. In addition it has been difficult to compose a set of conditions that is generally accepted as a dry weight standard.

A promising approach to assess the fluid status of a patient involves bioimpedance measurements. A low alternating current is applied to the patient using two or more electrodes, that are to be attached to the patient, and the corresponding difference of the electrical potential is measured. The various fluid compartments contribute differently to the measured signal. The usage of multiple frequencies allows to determine the intracellular volume (ICV) and the extracellular volume (ECV). To this end a typical model to analyze the bioimpedance measurement data includes a chain of sub-models. In a first step a spectrum, e.g. between 5 kHz and 1 MHz is applied and the complex impedances $$Z(j\omega) = \frac{u(j\omega)}{i(j\omega)}$$

are recorded for the spectrum, resulting in a semi-circle like curve in the complex impedance plane. As a next step or submodel the semicircular impedance spectrum is modelled using an equivalent circuit such as an equivalent circuit including a resistance $R_E$ modelling the extracellular current path and a resistance $R_I$ and a capacitor together modelling the intracellular current path. Also more complex equivalent circuits having more than one resistor/capacitor combination have been proposed. A suitable chain of submodels for determining the overhydration of a patient is described in "Modellbasiertes impedanzmessendes Assistenzsystem bei der Diagnose and Therapie von Mangelernährung"; VDI Verlag 2009, ISBN 978-3-18-327517-5.

Based on the determined electrical resistance $R_E$ and $R_I$ and anthropomorphic parameters like height h, weight m and body mass index BMI the extracellular volume (ECV) intracellular Volume (ICV) may be derived using the following formulas:

$$ECV = k_{ECV}\left(\frac{h^2\sqrt{m}}{R_E}\right)^{2/3}; kECV = \frac{0.188}{BMI} + 0.2883$$

$$ICV = k_{ICV}\left(\frac{h^2\sqrt{m}}{R_I}\right)^{2/3}; kICV = \frac{5.8758}{BMI} + 0.4194,$$

Based on the determined intracellular volume (ICV) and extracellular volume (ECV) it is possible to determine the hydration state in terms of an amount of excess fluid or a dehydration. One example of such an arrangement or device is described in the international patent application WO 2006/002685. This device also allows determining the body composition in respect to other volume compartments of the patient, in particular the fraction of lean and adipose tissue. Thus it is also possible to assess the nutrition status of a patient.

The above mentioned chain of models relies on a measurement which is based on multiple frequencies, requiring a relatively complex hardware equipment both for sweeping through the frequency spectrum and for analyzing the results of the measurement. Also the handling of the spectroscopic hardware equipment and the performing of the bioimpedance measurement usually requires the presence of trained staff. Therefore the models described above are mainly available for patients in clinics.

Therefore it is an object of the present invention to overcome this problem and to provide a method and a device for determining the hydration or nutrition status suitable for ambulatory patients.

SUMMARY

This and other objects are solved by a method for determining an overhydration parameter or a body composition parameter of a patient comprising: obtaining first bioimpedance measurement data of a patient from a first type of bioimpedance measurement, deriving bioimpedance calibration data from the first bioimpedance measurement data for calibrating second bioimpedance measurement data from a second type of bioimpedance measurement, obtaining the second bioimpedance measurement data from a second bioimpedance measurement of the patient and calibrating the second bioimpedance measurement data using the calibration data to determine the overhydration parameter or the body composition parameter of the patient.

The object of the invention is further solved, and advantageous embodiments thereof obtained, by the method, arrangement, and computer program product described and claimed below.

BRIEF DESCRIPTION OF THE DRAWINGS

Further details and advantages in accordance with the teaching of the present invention will be described in connection with the drawings.

FIG. 1 depicts an arrangement for determining a body composition parameter or an overhydration parameter from a combination of a first bioimpedance measurement and a second bioimpedance measurement, or in other words from a first bioimpedance measurement that is used to calibrate a second bioimpedance measurement.

Figure 1:
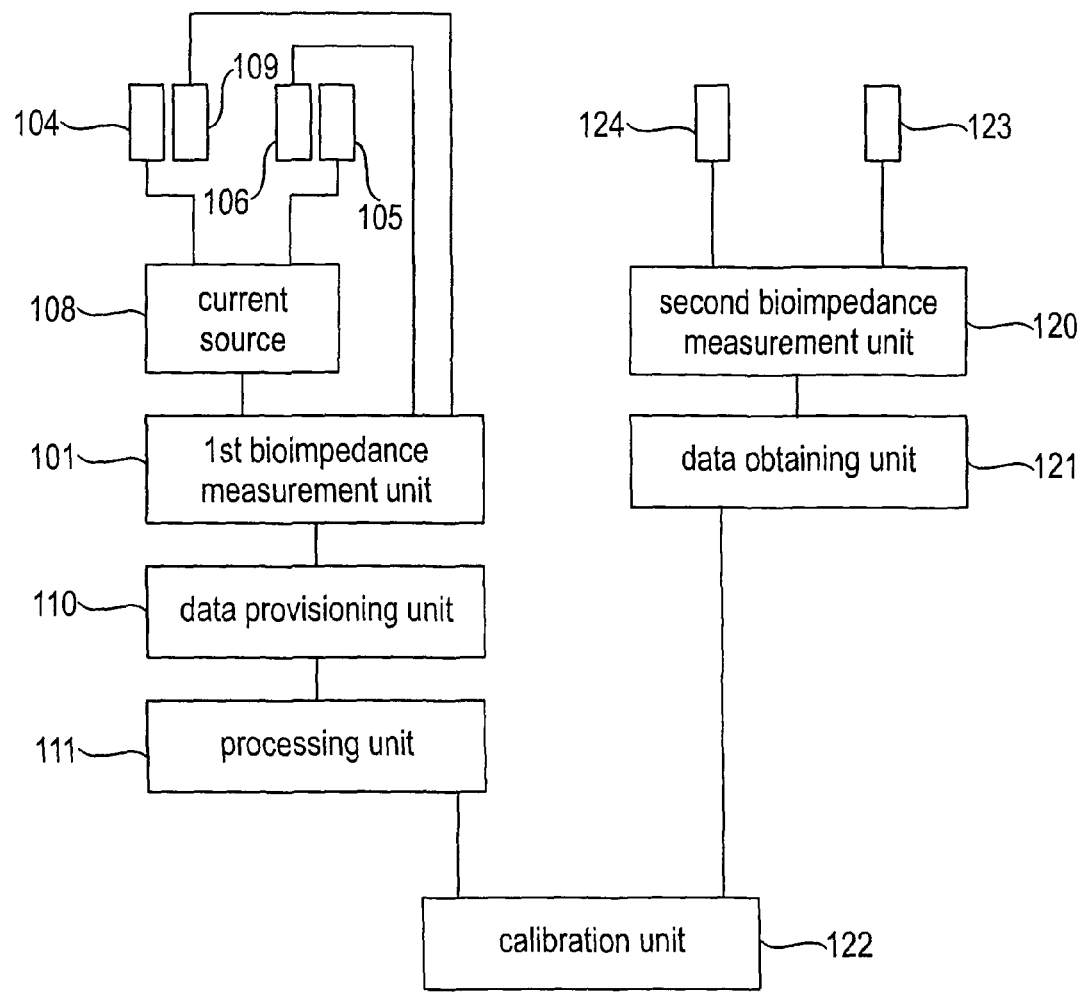
FIG. 1 is a block diagram depicting an arrangement for determining an overhydration parameter or a body composition parameter.

The arrangement of FIG. 1 comprises a first bioimpedance measurement unit 101 for performing a first bioimpedance measurement of a patient to obtain first bioim-pedance measurement data. To that end the first bioimpedance measurement unit 101 may comprise or be attached to a first and a second pair of electrodes, the first pair of electrodes being connected to a current source 108 and driving or predetermining a certain current between a first current electrode 104 and a second current electrode 105. The first 104 and the second 105 current electrode may be embodied such that they may be attached to the patient body at predetermined areas, such as at the wrist and at the ankle. Close to the current electrodes on the current path between the first 104 and the second 105 current electrode first 106 and second 109 voltage electrodes may be arranged, to record the voltage changes as the current between the current electrodes is sweeped through a predetermined frequency spectrum. This separate configuration of current electrodes and voltage electrodes is sometimes termed a four electrode configuration. The predetermined frequency spectrum may be e.g. the frequency spectrum between 5 kHz and 1 MHz or any other suitable frequency spectrum. By evaluating the relationship be-tween the driven or predetermined current between the first 104 and second 105 current electrode and the resulting voltage, which is measured between the first 108 and the second 109 voltage electrode a complex impedance spectrum may be determined and recoded within the first bioimpedance measurement unit 101 as is known in the art. The recoded complex impedance spectrum may be or may be comprised in first bioimpedance measurement data. Alternatively the complex impedance spectrum may be evaluated to obtain data derived from the complex impedance spectrum, e.g. an overhydration parameter or a body composition parameter may be derived from the complex impedance spectrum as has been described in relation to the background art. To derive an overhydration parameter or a body composition parameter further input data from the patient may be used such as height, weight, gender, the presence or absence of amputations or comorbidities and the like. In the context of the present invention bioimpedance measurement data may include immediate measurement results such as a recorded voltage between bioimpedance electrodes or a recorded complex bioimpedance spectrum as well as data derived from immediate measurement results such as an overhydration parameter or a body composition parameter derived from the recorded complex bioimpedance spectrum.

A data provision unit 110 for obtaining the bioimpedance measurement data is adapted to receive the first bioimpedance measurement data from the first bioimpedance measurement unit 101 and transmit the first bioimpedance measurement data further to the processing unit 111. The processing unit 111 is adapted to derive bioimpedance calibration data from the from the first bioimpedance measurement data which is suitable for calibrating second bioimpedance measurement data, which has been or is to be obtained from a second bioimpedance measurement of the patient, the second bioimpedance measurement being a bioimpedance measurement of a second type. The second bioimpedance measurement may be performed using bioimpedance spectroscopy or the second bioimpedance measurement may be performed using a bioimpedance measurement using a limited number of frequencies (typically three or four) or using only a single frequency. The second bioimpedance measurement may be performed using the second bioimpedance measurement unit 120, which is connected to pair of electrodes 124, 123, for contacting the human body at different regions, between which the bioimpedance is to be measured. In one example the electrodes 124, 123 are connectable to the right and the left hand respectively, in another example the electrodes 124, 123 are connectable to the right and the left foot. This configuration applying a pair of electrodes for the bioimpedance measurement is termed two electrode configuration. Alternatively a four electrode configuration separating the electrodes for predetermining a current and the electrodes for measuring a voltage could be applied.

The second bioimpedance measurement is advantageously a bioimpedance measurement that has at least one property different to the first bioimpedance measurement, e.g. the first bioimpedance measurement is a bioimpedance measurement using bioimpedance spectroscopy and the second bioimpedance measurement is a bioimpedance measurement using a limited number or only a single frequency for determining the complex impedance.

A data obtaining unit 121 is operable to receive the second bioimpedance measurement data and pass it over to the calibration unit 122 suitable for calibrating the second bioimpedance measurement data using the bioimpedance calibration data.

The bioimpedance calibration data functions to calibrate the second bioimpedance measurement data, such that an overhydration parameter or a body composition parameter can be derived from the second bioimpedance measurement data which is combined with or in other words calibrated using the bioimpedance calibration data. By this the significance of the second bioimpedance measurement data may be enhanced, e.g. the second bioimpedance measurement data may not be significant enough to derive a body composition parameter or a overhydration parameter by evaluating only the second bioimpedance measurement data, however, the second bioimpedance measurement data may be significant enough, such that from the second bioimpedance measurement data taken in combination with the bioimpedance calibration data a body composition parameter or a overhydration parameter may be derived.

How bioimpedance measurement data may be calibrated to obtain an overhydration parameter or a body composition parameter will be described in relation to FIG. 2.

Figure 2:
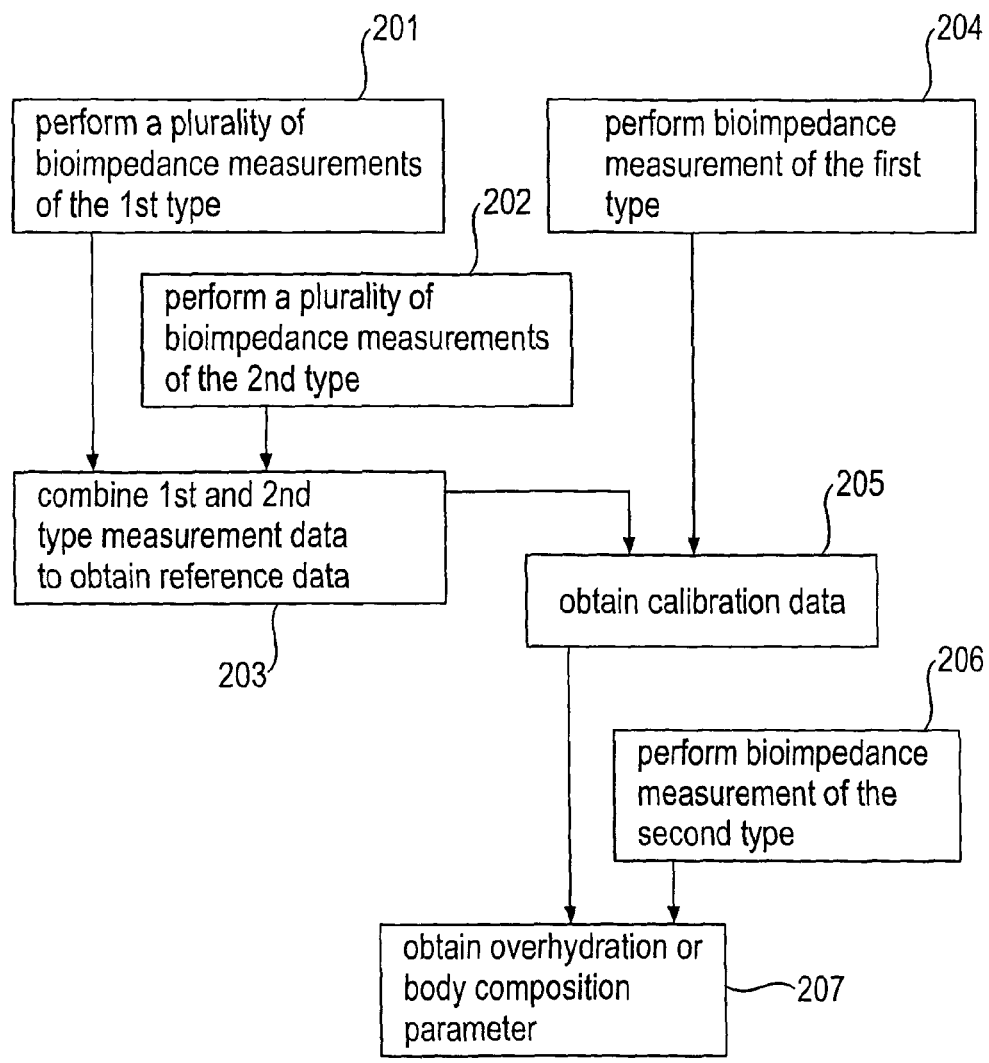
FIG. 2 is a flow diagram depicting a succession of steps to calibrate bioimpedance measurement data to obtain an overhydration parameter or a body composition parameter.

The method of FIG. 2 comprises a step 201 of performing a plurality of bioimpedance reference measurements of a first type of bioimpedance measurement and a step 202 of performing a plurality of second bioimpedance reference measurements of a second type. The plurality of first type of bioimpedance reference measurements are correlated with the plurality of second type of bioimpedance reference measurements to obtain bioimpedance reference data in a correlation step 203. In the context of the description of FIG. 2 the terms first type of bioimpedance measurement and second type of bioimpedance measurement shall be understood in the same sense in which those terms have been introduced in accordance with the description of FIG. 1.

A bioimpedance measurement of the first type and a bioimpedance measurement of the second type necessary for generating bioimpedance reference data may be performed for a reference population, e.g. a population of dialysis patients. This may be done in a way that each of the individuals of the reference population is measured using the first type of bioimpedance measurement and at the same event also measured using the second type of bioimpedance measurement, e.g. each time a dialysis session is performed for the patient.

The correlation step may be performed in a way that the first type of bioimpedance measurement may be significant enough to determine a body composition parameter or an overhydration parameter from the first bioimpedance reference measurement. For example the first type of bioimpedance measurement may be a bioimpedance spectroscopy and the models described above in relation to the related art may be used to determine the overhydration or body composition parameter. The overhydration or body composition parameter may be derived each time a first type of bioimpedance measurement is determined for a certain patient. First type of bioimpedance measurement data may be e.g. a complex impedance spectrum taken between a first and a second frequency e.g. between 5 kHz and 1 MHz.

At the same event as the first type of bioimpedance measurements are performed second bioimpedance measurements may be performed. The second bioimpedance measurement data may not be significant enough to determine an overhydration parameter or a body composition parameter from the second type of bioimpedance measurement alone, at least not in absolute quantities and not if taken without additionally using calibration data. The second type of bioimpedance measurement data may be data from a single frequency bioimpedance measurement, e.g. a complex impedance for a certain frequency.

The first type of bioimpedance measurement data are then in a correlation step 203 correlated with the second type of bioimpedance measurement data, to obtain bioimpedance reference data, e.g. a function describing the overhydration or body composition parameter dependent from a current second type of bioimpedance measurement in combination with an earlier first type of bioimpedance reference measurement.

Data from a first type of bioimpedance reference measurement performed earlier in a step 204 may then in a combination step 205 be combined with the bioimpedance reference data, to obtain bioimpedance calibration data, the bioimpedance calibration may have the format of a function describing the overhydration parameter in dependence from the second type of bioimpedance measurement.

E.g. the second bioimpedance measurement may be a single frequency bioimpedance measurement taken at a certain high frequency e.g. 50 kHz and data obtained using the second bioimpedance measurement may be the complex impedance taken at that certain frequency, e.g. the complex impedance taken at 50 kHz, which may be termed $Z_{50\ kHz}$. The calibration data then could have the function of on overhydration or other body composition parameter in dependence from the complex impedance taken at that single high frequency, such as 50 k Hz and in addition an anthropomorphic measure. An anthropomorphic measure could be the height or the weight, advantageously the height and weight taken in combination. Thus the calibration data could have the function of an overhydration parameter in dependence from the complex impedance $Z_{50\ kHz}$ taken at 50 kHz taken in combination with the height and the weight of the patient.

Another scenario for a suitable format of the calibration data could be that during the first type of bioimpedance measurement the complex spectrum of the impedance is determined and in addition the complex impedance is determined at a single frequency. From the complex spectrum and some anthropomorphic measure the overhydration or another body composition parameter may be derived as is known in the art. The calibration data could be comprised of a combination of the overhydration or body composition parameter and the single frequency complex impedance.

The second bioimpedance measurement subsequently taken at the same single frequency as the previous single frequency measurement, could then be used to derive an impedance difference to the previous single frequency measurement and the overhydration or body composition parameter can then be modified using the impedance difference.

Another format of the calibration data would be the format of the overhydration or body composition parameter, which could be modified in accordance with the second type of bioimpedance measurement, which could be the complex impedance measured at a certain frequency such as 50 kHz. To determine an actual body composition parameter in this example a ratio of an absolute value of a current complex impedance and a reference complex impedance determined earlier could be considered to correspond to the ratio between the actual and the earlier determined body composition parameter:

$$\frac{OH_{act}}{OH_{ref}} = \left|\frac{Z_{50act}}{Z_{50ref}}\right|,$$

wherein is the overhydration parameter determined earlier using a reference measurement, $Z_{50\ ref}$ is the complex impedance determined earlier in a reference measurement and $Z_{50\ act}$ is the complex impedance determined in an actual bioimpedance measurement.

The ratio of the earlier determined overhydration or body composition parameter and the earlier determined absolute value of complex impedance measured at a single frequency $$\frac{OH_{ref}}{|Z_{50ref}|}$$

could then be considered bioimpedance calibration data, and the actual overhydration or body composition could be determined using an actual bioimpedance measurement using the formula:

$$OH_{act} = \frac{OH_{ref}}{|Z_{50ref}|}|Z_{50act}|.$$

As an alternative to absolute values of complex impedances real parts or imaginary parts of complex impedances could be considered.

The first type of bioimpedance reference measurement may be a first type of bioimpedance reference measurement taken for a particular patient for example each time the particular patient visits the clinic for performing a dialysis session or every nth time the patient visits the clinic for performing a dialysis session.

A second type of bioimpedance measurement may then be performed at a measurement step 206 and the second type measurement data obtained in a measurement step 206 may then be combined with bioimpedance calibration data obtained in step 205 to obtain an overhydration parameter or a body composition parameter in step 207.

A usage scenario could be that a for a particular patient second type of bioimpedance measurements could be performed at every dialysis session, e.g. every time a dialysis patient visits the dialysis clinic for a dialysis session and first type of bioimpedance measurements to generate reference data could be performed every nth time the dialysis patient visits the dialysis clinic, n being an integer, preferable in the range between 3 and 10. By this more sophisticated measurement equipment for performing a first type of dialysis measurement could be better utilized.

In accordance with another usage scenario the patient is an ambulatory patient performing a home dialysis, such as a peritoneal dialysis, and the second type of bioimpedance measurement is performed daily or every time the patient undergoes a home dialysis treatment. Less frequently the patient visits a dialysis clinic for per-forming a general evaluation of the clinical state and at those visits the first type of bioimpdance measurements are performed.

By this an accurate status of the overhydration or body composition parameter may be obtained with a high frequency for ambulatory patients.

According to both these usage scenarios second type of bioimpedance measurement data will be taken more frequently than first type of bioimpedance measurement data.

For both usage scenarios the patient status could be monitored over time in the following way: Over time a plurality of bioimpedance measurements of the second type are performed at different times to generate a time series of bioimpedance measurements. For this time series of second type of bioimpedance measurement data a time analysis is performed to determine whether a current bioimpedance measurement of the time series deviates significantly from previous bioimpedance measurements of the time series. If so a message could be generated to alert the patient or to indicate to the patient that a new measurement of the first type of bioimpedance measurements should be performed.

To perform a time series analysis the complex plane of the measured bioimpedance could be considered in a complex plane having a rotated axis, as will be described further below in relation to FIGS. 10 and 11.

Figure 3:
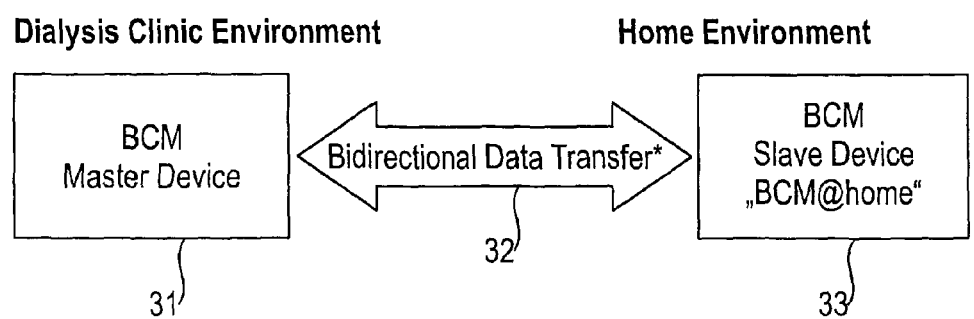
FIG. 3 is a block diagram depicting a first and a second bioimpedance measurement device.

FIG. 3 is a block diagram depicting a first bioimpedance measurement device 31 for performing first type a bioimpedance measurement and a second bioimpedance measurement device 33 for performing a second type of bioimpedance measurement.

In the context of the description of FIG. 3 the terms first type of bioimpedance measurement and second type of bioimpedance measurement shall be understood in the same sense in which those terms have been introduced in accordance with the description of FIG. 1.

The first bioimpedance measurement device 31, which is termed 'BCM master device' in FIG. 3 may be used in a dialysis clinic environment and may be suitable to perform the first type of bioimpedance measurements, the generation of calibration data and other processing of first type of bioimpedance measurements as have been described above in relation to description of FIG. 2.

The second bioimpedance measurement device which is termed 'BCM slave device' or 'BCM @ home' in FIG. 3 may be used in a home environment of an ambulatory patient and may be suitable to perform the second type boimpedance measurements, the processing of calibration data, the determination of an overhydration or body composition parameter and other data processing of second type of bioimpedance measurements as has been described above in relation to the description of FIG. 2.

A bi-directional data transfer 32 is provided between the first 31 and the second 33 bioimpedance measurement device to allow transmission of calibration data from the first bioimpedance measurement device 31 to the second bioimpedance measurement device and other data exchange between the first and the second bioimpedance measurement device as has been described above in relation to FIG. 2.

Advantageously among the other data exchange is a transfer of current and past bioimpedance measurement data from the second bioimpedance measurement device 33 to the first bioimpedance measurement device 31 to allow improving bioimpedance reference data at the first bioimpedance measurement device or at a network computer connected to the first bioimpedance measurement device (not shown). The bi-directional data transfer may be embodied as a data transmission over a cable, as a wireless transmission, via a USB (universal serial bus) card, via a card, such as the patient card, or in a way that both the first and the second bioimpedance measurement device are connected subsequently to a same third device (e.g. a database) such that in effect data is transmitted between the first 31 and the second 32 bioimpedance measurement device.

In the latter case of a database providing the transmission of data between the first 31 and the second 33 bioimpedance measurement device the database could also collect the first and the second bioimpedance measurement data, to obtain both bioimpedance calibration data and bioimpedance reference data and to provide the bioimpedance calibration data to the second biompedance measurement device.

Figure 4:
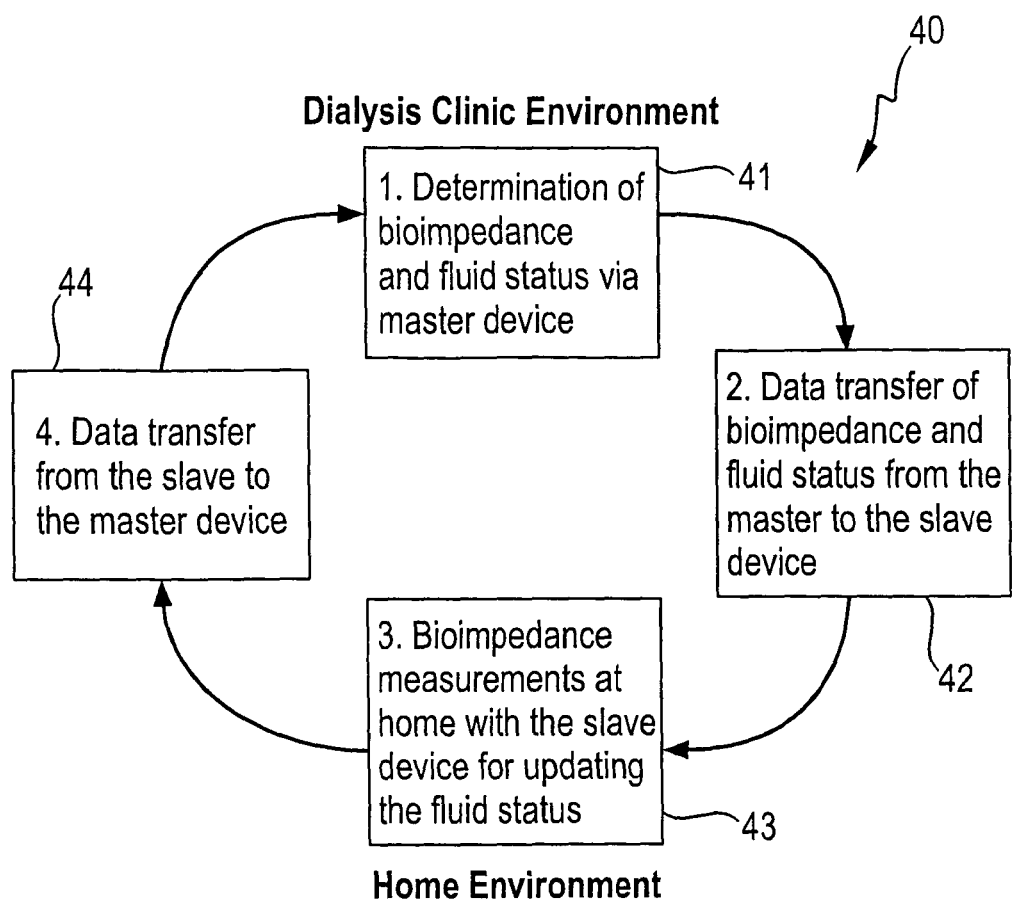
FIG. 4 is a flow diagram depicting processing steps related to bioimpedancce measurements of a patient moving between a home environment and a dialysis clinic environment.

A succession of processing steps of a method 40 repeatedly iterated for a patient moving between a dialysis clinic environment and a home environment is depicted in FIG. 4. In the context of FIG. 4 the terms first type of bioimpedance measurement and second type of bioimpedance measurement, bioimpedance calibration data, and bioimpedance reference data shall be understood in the same sense as has been disclosed above in relation to the description of FIGS. 1 and 2.

The method 40 starts with measurement step 41 to perform first type of bioimpedance measurement or bioimpedance reference measurement of a patient in a dialysis clinic environment to obtain first type of bioimpedance measurement data and derive a fluid status or other body composition parameter from the first type of bioimpedance measurement or bioimpedance reference measurement.

In a subsequent data transmission step 42 either the first type of bioimpedance measurement data or data derived from the first type of bioimpedance measurement data including bioimpedance calibration data is transferred from the dialysis clinic environment to the home environment. The transfer of data can be by a physical storage element, like a patient card, that the patient takes with him or her, or the data transfer can be a transfer between a bioimpedance measurement device or other device in the dialysis clinic environment and a bioimpedance measurement device or other device in the home environment via a data network connection.

In the home environment a processing step 43 is performed including bioimpedance measurement of a second type is performed to obtain second type of bioimpedance measurement data. In the home environment the bioimpedance calibration data and the second type of bioimpedance measurement data may be combined to derive or update a overhydration or other body composition parameter of the patient.

Subsequently the second type of bioimpedance measurement data is transferred in a transfer step 44 from the home environment to the dialysis clinic environment, where it may be processed to improve bioimpedance reference data.

Figure 5:
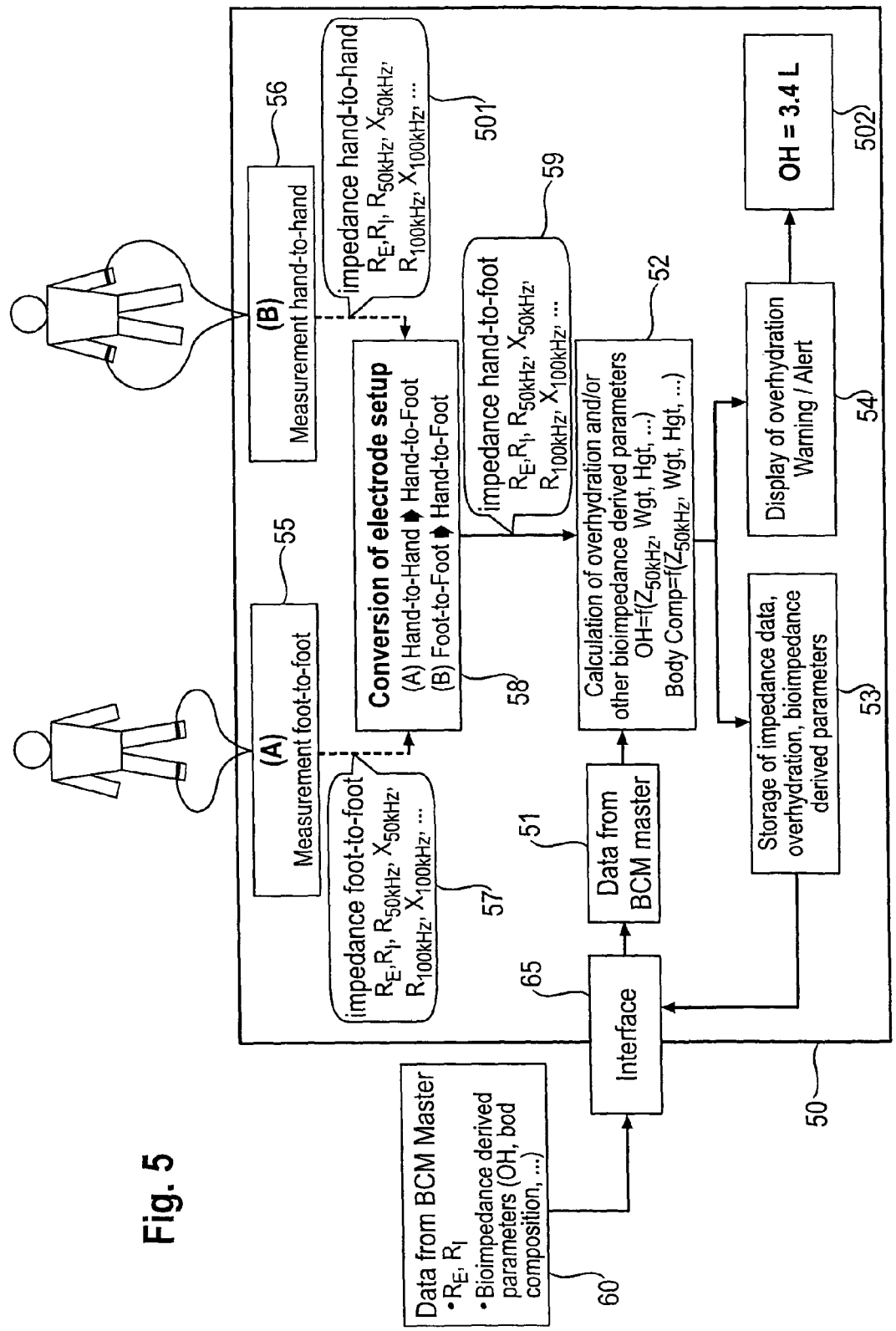
FIG. 5 is a block diagram of a bioimpedance measurement device.

A possible configuration of a bioimpedance measurement device is depicted in FIG. 5. In the context of FIG. 5 the terms first type of bioimpedance measurement and second type of bioimpedance measurement, bioimpedance calibration data, and bioimpedance reference data shall be understood in the same sense as has been disclosed above in relation to the description of FIGS. 1 and 2.

The bioimpedance measurement device 50 comprises a first 55 and a second 56 bioimpedance measurement unit. The first 55 and the second 56 bioimpedance measurement unit connect to bioimpedance electrodes that are attachable to a patient for performing bioimpedance measurements. Both the first 55 and the second 56 bioimpedance measurement unit include or connect to a source for generating a predetermined current at a predetermined high frequency between connected electrodes and a voltage measurement unit (not shown) for measuring the resulting voltage difference to determine the complex impedance between the bioimpedance electrodes. Although depicted as separate entities, the first 55 and the second 56 bioimpedance measurement unit could utilize common hardware, i.e. a common current source and a common voltage measurement unit. Both the first 55 and the second 56 bioimpedance measurement unit could apply a two electrode configuration or a four electrode configuration.

The predetermined frequency may be selectable, appropriate exemplary values may be 50 kHz or 100 kHz. The first 55 and the second 56 interface thus generate single frequency bioimpedance measurement data 57 or 501 including a real, an imaginary or a complex impedance value for a certain high frequency e.g. $R_{50kHz}$, $R_{100kHz}$, $X_{50kHz}$, $X_{100kHz}$, $Z_{50kHz}$, or $Z_{100kHz}$ alternatively the bioimpedance measurement data may be complex impedances of a model used to interpret the bioimpedance such as the extracellular resistance $R_E$, and the intracellular resistance $R_I$.

In one embodiment the bioimpedance measurement data is converted between a first and a second format using a conversion factor considering a first type of electrode setup and a second type of electrode setup in a conversion unit 58. This may be suitable when the biompedance measurement data may be combined with or compared to other bioimpedance measurement data.

For example the bioimpedance measurement performed using the bioimpedance measurement device 50 may perform a second type of biompedance measurement in accordance with what has been disclosed in relation to FIGS. 1 and 2 and it is desirable to compare or combine bioimpedance measurement data from the second type of bioimpedance measurement with bioimpedance measurement data from the first type of bioimpedance measurement.

Accordingly the bioimpedance measurement of the first type may involve a first type of electrode configuration and the bioimpedance measurement of the second type may involve a second type of electrode configuration. E.g. typically a bioimpedance measurement performed at multiple frequencies involves a hand-to-foot configuration of electrodes and a bioimpedance measurement performed at a single frequency involves a hand-to-hand or a foot-to foot configuration of the electrodes.

To make bioimpedance measurement data obtained using the first and the second electrode configuration comparable or combinable a conversion unit 58 is provided that allows a conversion between a format of bioimpedance measurement data obtained using a first type of electrode configuration and a format of bioimpedance measurement data obtained using second type of electrode configuration.

The conversion may be e.g. from a format considering a measurement using a foot-to-foot or a hand-to-hand configuration to a format considering a measurement using a hand-to-foot configuration.

The bioimpedance measurement data thus obtained may have the format of a real part R and imaginary part X of an impedance value for a certain high frequency e.g. $R_{50kHz}$, $R_{100kHz}$, $X_{50kHz}$, or $X_{100kHz}$, alternatively the format of complex impedances of a model used to interpret the bioimpedance such as the extracellular resistance $R_E$, and the intracellular resistance $R_I$.

The bioimpedance data 59 thus obtained is provided to a processing unit 52 for calculating an overhydration or other body composition parameter based on the bioimpedance measurement data 59 and the bioimpedance calibration data 51.

To that end the processing unit 52 is configured to receive bioimpedance calibration data 51 via the bi-directional interface 65 connecting to a data source 60. The data source 60 includes calibration data that has been obtained using bioimpedance measurement data from a bioimpedance measurement of the first type as has been described above in relation to FIGS. 1 and 2.

Processing results obtained in the processing unit 52 are stored in the storage unit 53 and, via the bi-directional interface 65 fed back to the data source 60, where they support improving the bioimpedance reference data.

Display of processing results may be controlled by the display control unit 54 and displayed on display 502.

A time series analysis of the processing results may be performed in the processing unit 52 to analyse obtained processing results to determine whether a current bioimpedance measurement or derived overhydration or body composition parameter deviates significantly from previous bioimpedance measurements or derived overhydration or body composition parameter. When a significant deviation exists, this may be indicated to the display control unit 54 and displayed on display 502.

Figure 6:
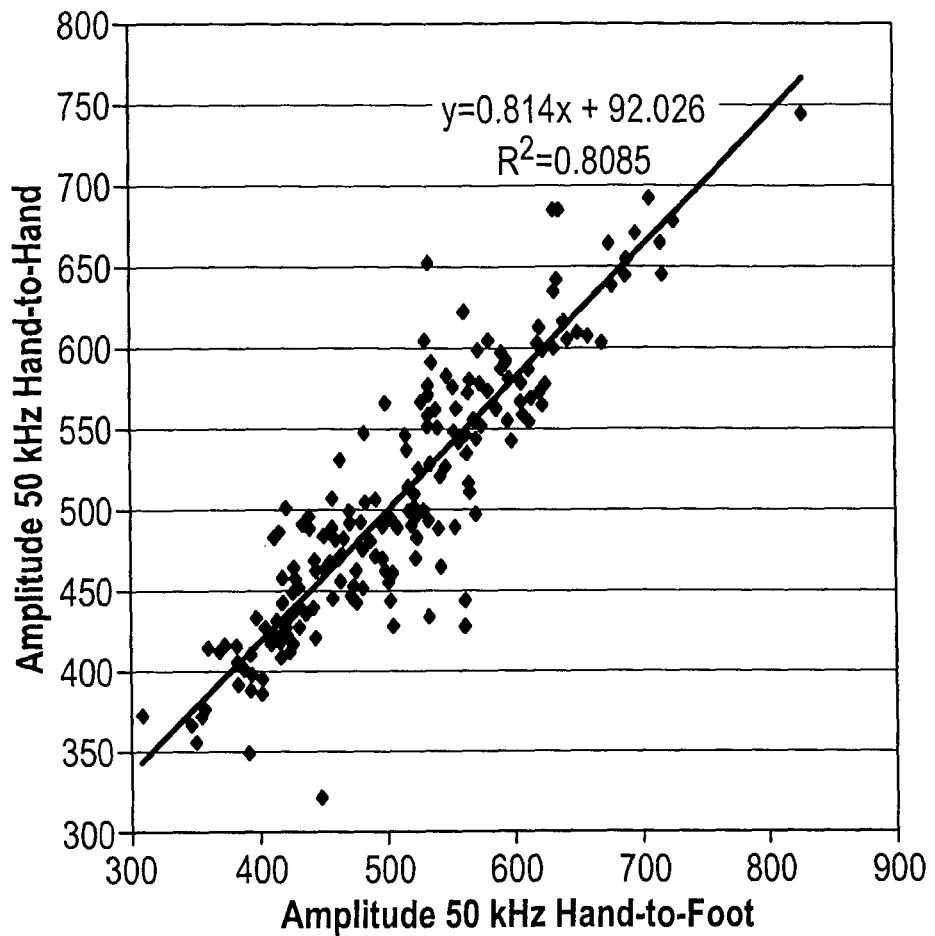
FIG. 6 is a diagram depicting a conversion of amplitude values between electrode configurations.

FIG. 6 depicts a relationship between amplitudes of a complex impedance for a conversion between a format of a bioimpedance measurement considering a hand-to-foot configuration to a format considering a hand-to-hand configuration. Each dot represents a particular measurement comprising a bioimpedance amplitude value obtained using a hand-to-hand configuration and a bioimpedance amplitude value obtained using a hand-to-foot configuration. Both measurements have been taken at the same high frequency, which is 50 kHz in the present example.

The horizontal or x-axis corresponds to the hand-to-foot configuration and the vertical or y-axis corresponds to the hand-to-hand configuration. A linear fit is represented by the formula on the upper right side. The value for $R^2$ represents the coefficient of determination of the linear fit.

Figure 7:
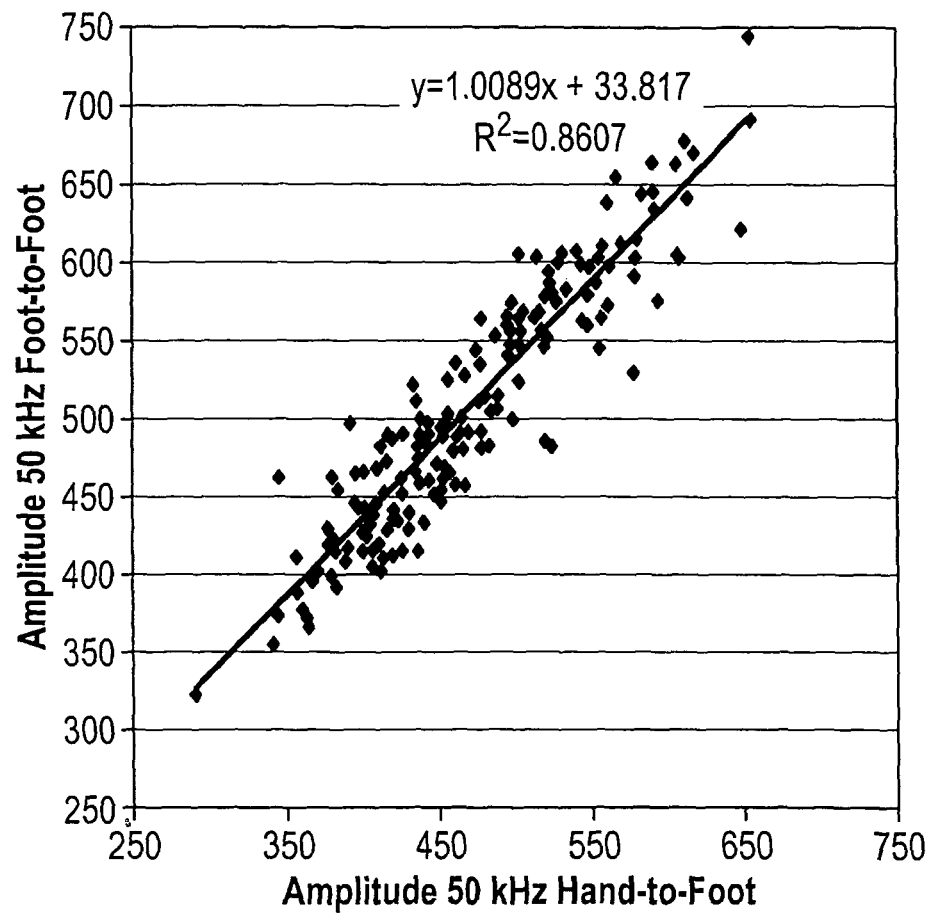
FIG. 7 is another diagram depicting another conversion of amplitude values between electrode configurations.

FIG. 7 represents an amplitude relationship for a conversion between a hand-to-foot electrode configuration and a foot-to-foot electrode configuration, similar to the amplitude relationship of FIG. 6 described above.

Figure 8:
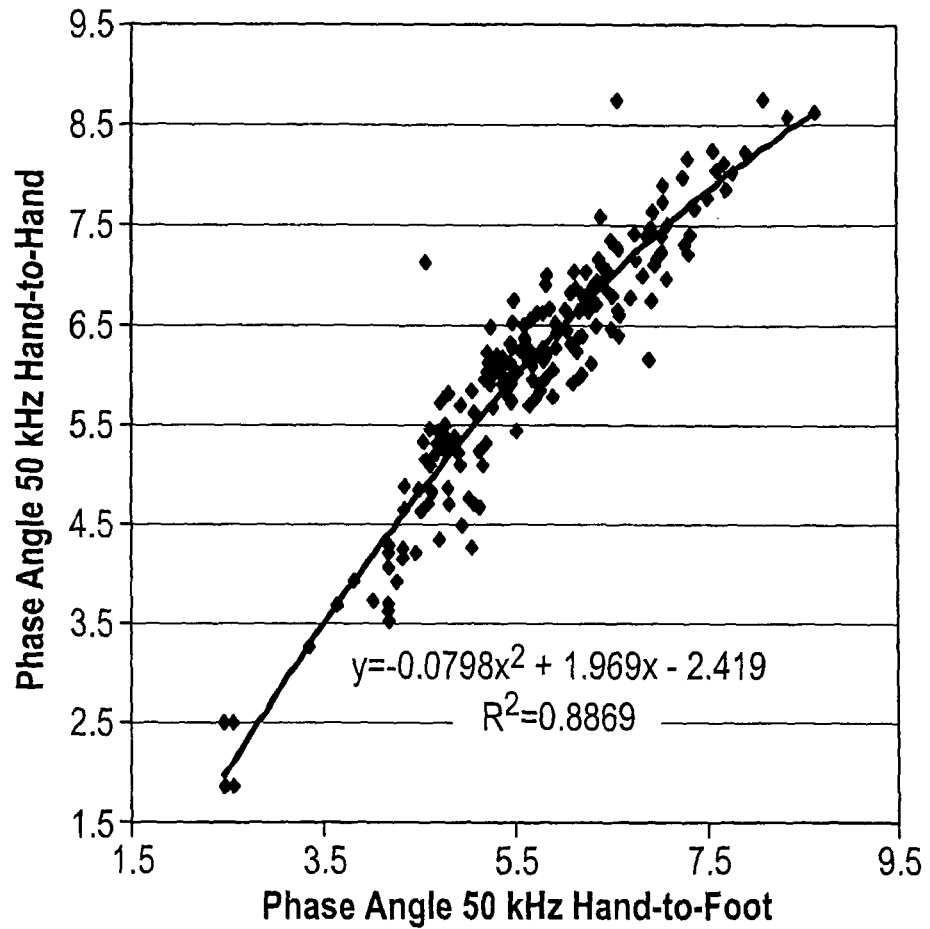
FIG. 8 is a diagram depicting a conversion of phase angle values between electrode configurations.

FIG. 8 depicts a relationship between phases of a complex impedance for a con-version between a format of bioimpedance measurement considering a hand-to-foot configuration to a format considering a hand-to-hand configuration. Each dot represents a particular measurement comprising an bioimpedance phase value obtained using a hand-to-hand configuration and a bioimpedance amplitude value obtained using a hand-to-foot configuration. Both measurements have been taken at the same high frequency, which is 50 kHz in the present example.

The horizontal or x-axis corresponds to the hand-to-foot configuration and the vertical or y-axis corresponds to the hand-to-hand configuration. A square fit is represented by the formula. The value for $R^2$ represents the coefficient of determination of the square fit.

Figure 9:
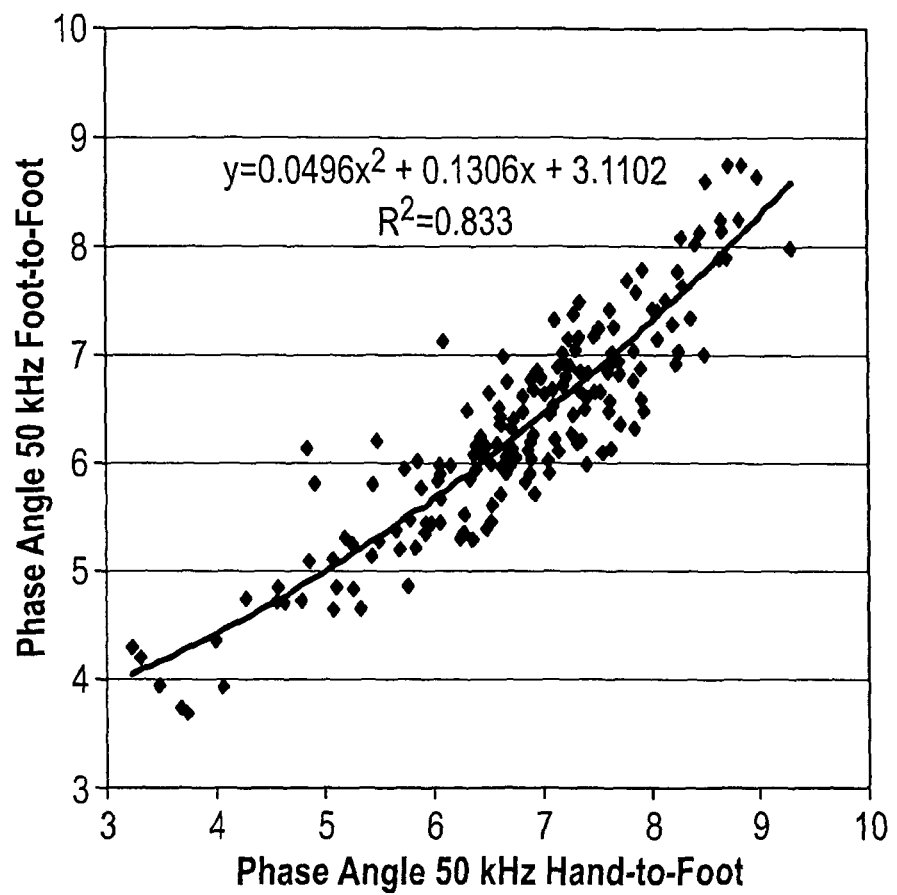
FIG. 9 is another diagram depicting another conversion of phase angle values between electrode configurations.

FIG. 9 represents a phase relationship for a conversion between a hand-to-foot electrode configuration and a foot-to-foot electrode configuration, similar to the phase relationship of FIG. 8 described above.

Figure 10:
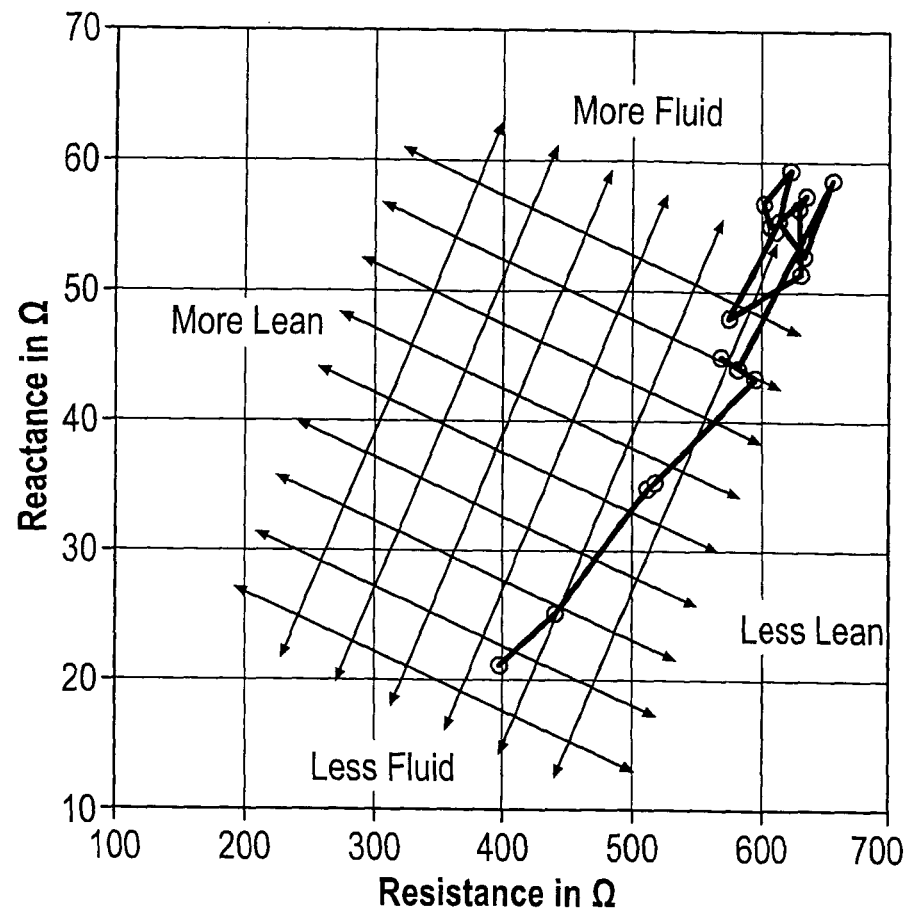
FIG. 10 is a time series of the evolution of the impedance in the complex plane for a single frequency impedance measurement.

FIG. 10 depicts the timely evolution of the complex impedance measured at a certain single frequency, e.g. at 50 kHz, at succeeding points in time for a particular patient. The real part of the complex impedance noted as resistance is depicted on the horizontal axis and the imaginary part of the complex impedance is noted as reactance and is depicted on the vertical axis. A rotated coordinate system has a first axis between a less lean region and a more lean region and second axis between a less fluid and a more fluid region. Changes of the impedance projected on the axis between the less fluid and the more fluid region can be attributed to changes of the fluid status, whereas changes of the impedance projected on the axis between the less lean region and the more lean region can be attributed to changes of the body composition. It can be seen that the particular patient depicted in FIG. 10 mainly undergoes a change in the fluid status.

Figure 11:
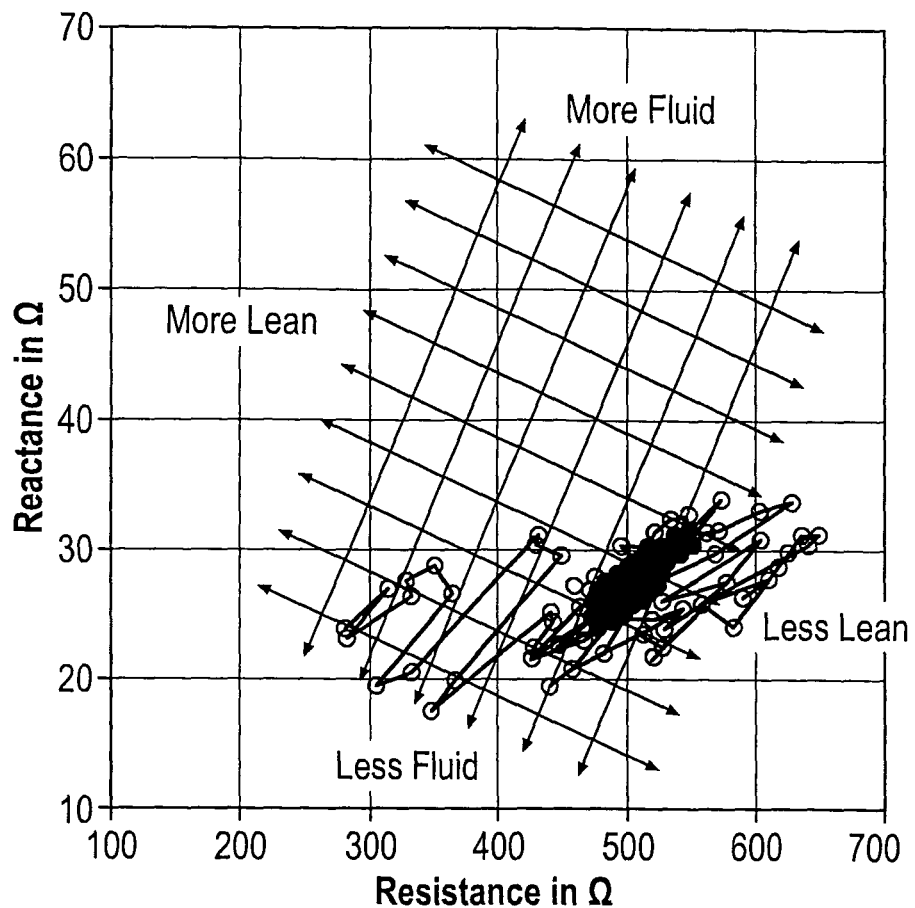
FIG. 11 is a further time series of the evolution of the impedance in the complex plane for another single frequency impedance measurement.

FIG. 11 depicts a timely evolution of the complex impedance measured at a single frequency for another patient at succeeding points in time. The meaning of the real and imaginary part of the complex impedance as well as the meaning of the rotated coordinate system attributing changes in impedance to fluid status or body composition corresponds to what has been described in relation to FIG. 10. It can be seen that the patient depicted in FIG. 11 undergoes a change in the body composition.

A time series analysis performed on the evolution of the impedance over time may consider a projection on the first and the second axis described. Thus a warning indicating a significant change of the measured impedance may differentiate be-tween a change in body composition and a change of the fluid status.

The invention claimed is:

1. Method of correcting bioimpedance measurement data obtained from a second type of bioimpedance measurement unit for determining and updating an overhydration parameter or a body composition parameter of a patient comprising the steps of:

performing a first type of bioimpedance measurement of a patient using a first type of bioimpedance measurement unit and thereby obtaining first bioimpedance measurement data of the patient, performing a second type of bioimpedance measurement of the patient using a second type of bioimpedance measurement unit and thereby obtaining second bioimpedance measurement data of the patient, deriving bioimpedance correction data from the first bioimpedance measurement data and the second bioimpedance measurement data transferring the bioimpedance correction data to a further bioimpedance measurement device containing a further second type of bioimpedance measurement unit, performing a further second type of bioimpedance measurement of the patient using the further second type of bioimpedance measurement unit to obtain further second bioimpedance measurement data of the patient, and correcting the further second bioimpedance measurement data using the transferred bioimpedance correction data to determine an overhydration parameter or body composition parameter of the patient.

2. Method according to claim 1, wherein the step of performing the first type of bioimpedance measurement comprises measuring a bioimpedance spectrum of the patient at multiple frequencies.

3. Method according to claim 2, wherein the step of performing the second type of bioimpedance measurement comprises measuring a bioimpedance of the patient at a single frequency.

4. Method according to claim 1, further comprising obtaining a plurality of the further second type of bioimpedance measurements at different times to generate a time series of bioimpedance measurements, performing time analysis of the time series to determine whether a current further bioimpedance measurement of the time series deviates significantly from previous further bioimpedance measurements of the time series, and when a deviation is determined generating one of an indication that first type of bioimpedance measurement should be performed anew or a warning message.

5. Method according to claim 1, wherein the step of deriving the correction data comprises using bioimpedance reference data correlating results of the first type of bioimpedance measurement and results of the second type of bioimpedance measurement.

6. Method according to claim 5, further comprising a step of deriving the reference data by applying a conversion factor between a first format considering a measurement using a first type of electrode configuration and a second format considering a measurement using a second type of electrode configuration, wherein the first type of bioimpedance measurement comprises the first type of electrode configuration, and wherein the second type of bioimpedance measurement comprises the second type of electrode configuration.

7. Computer program product comprising, recorded on a computer readable medium, computer program portions coded to perform the method of claim 1 when under control of a computer running the program.

8. Arrangement for correcting bioimpedance measurement data obtained by a second type of bioimpedance measurement unit for determining an overhydration parameter or a body composition parameter of a patient comprising:
- a first type of bioimpedance measurement unit adapted for performing a first type of bioimpedance measurement of a patient;
- a second type of bioimpedance measurement unit adapted for performing a second type of bioimpedance measurement of a patient;
- a combination unit adapted for deriving bioimpedance correction data from the first bioimpedance measurement data and the second bioimpedance measurement data, and for transferring the bioimpedance correction data to a correction unit;
- wherein the correction unit is adapted for correcting a further second type of second bioimpedance measurement data obtained using a further second type bioimpedance measuring unit using the bioimpedance correction data for determining the overhydration parameter or the body composition parameter of the patient.

9. Arrangement according to claim 8, wherein the first type of bioimpedance measurement unit is adapted to measure the bioimpedance spectrum of the patient at multiple frequencies.

10. Arrangement according to claim 8, wherein the second bioimpedance measurement unit is adapted to measure the bioimpedance of the patient at a single frequency.

* * * * *